US006437122B2

(12) United States Patent
Shoji et al.

(10) Patent No.: US 6,437,122 B2
(45) Date of Patent: Aug. 20, 2002

(54) METHOD FOR PRODUCING A HETEROCYCLIC NITRILE

(75) Inventors: Takayuki Shoji; Mitsuhide Matsubara; Manabu Kimura; Yasuhiro Shiomi, all of Jyoto-ku (JP)

(73) Assignee: Koei Chemical Company, Limited, Osaka (JP)

( * ) Notice: Subject to any disclaimer, the term of this patent is extended or adjusted under 35 U.S.C. 154(b) by 0 days.

(21) Appl. No.: 09/735,900

(22) Filed: Dec. 14, 2000

(30) Foreign Application Priority Data

Dec. 17, 1999 (JP) ............................. 11-359993

(51) Int. Cl.$^7$ .................. C07D 251/14; C07D 239/24; C07D 241/04; C07D 215/02; C07D 213/02
(52) U.S. Cl. ................. 544/180; 544/182; 544/242; 544/336; 546/134; 546/330
(58) Field of Search ................... 544/88, 180, 182, 544/336, 242; 546/134, 330

(56) References Cited

U.S. PATENT DOCUMENTS

| | | | |
|---|---|---|---|
| 2,680,742 A | | 6/1954 | Scudi et al. ............. 260/294.9 |
| 2,945,862 A | * | 7/1960 | Mignonne et al. .......... 549/362 |
| 4,500,721 A | * | 2/1985 | Yamachika et al. ......... 549/362 |
| 5,646,288 A | * | 7/1997 | Siegrist et al. ............ 546/315 |

FOREIGN PATENT DOCUMENTS

| | | |
|---|---|---|
| DE | 228971 | 10/1985 |
| EP | 0613888 | 9/1994 |
| JP | 8183772 | 7/1996 |

OTHER PUBLICATIONS

Brown T. H. et al: Isocytosine H2–Receptor Histamine Antagonists. IV. The Synthesis and Biological Activity of Donetidine (SK&F93574) and Related Compounds; European Journal of Medicinal Chemistry, Chimica Therapeutica, Fr. Editions Scientificque Elsevier, Paris, vol. 28, No. 7/08, 1993, pp. 601–608.

Bennett L. R.: "Antihypertensive Activity of 6–Acrylpyridou2.3–Dpyrimidine–7–Amine Derivatives"; Journal of Medicinal Chemistry, US, American Chemical Society, Washington, vol. 24, No. 4, Apr. 1, 1981, pp. 382–389.

* cited by examiner

*Primary Examiner*—Richard L. Raymond
*Assistant Examiner*—Venkataraman Balasubramanian
(74) *Attorney, Agent, or Firm*—Stevens, Davis, Miller & Mosher, L.L.P.

(57) ABSTRACT

A method for producing a heterocyclic nitrile in high yield by a gas-phase catalytic reaction of a heterocyclic carboxylic acid or an ester thereof with ammonia in the presence of a catalyst comprising an oxide of at least one element selected from copper and zinc, and an effective method for producing a heterocyclic aldehyde, using the heterocyclic nitrile thus obtained as a starting material, are provided.

7 Claims, No Drawings

METHOD FOR PRODUCING A HETEROCYCLIC NITRILE

BACKGROUND OF THE INVENTION

The present invention relates to a method for producing a heterocyclic nitrile by a reaction of a heterocyclic carboxylic acid or an ester thereof with ammonia.

So far, as a method for producing a heterocyclic nitrile by a reaction of a heterocyclic carboxylic acid or an ester thereof with ammonia, a method is known in which 6-methylnicotinate and ammonia are reacted to produce 2-methyl-5-cyanopyridine in the presence of phosphorus oxychloride- [Izv. Akad. Nauk kaz. SSR, Ser. Khim. (1977), 27(5), 89–90].

Yield of 2-methyl-5-cyanopyridine in the known method is, however, only 35%, and a method in which a heterocyclic nitrite can be produced in a higher yield has been desired.

An object of the present invention is to provide a method in which a heterocyclic nitrile can be produced in a higher yield and a higher selectivity ratio by a reaction of a heterocyclic carboxylic acid or an ester thereof with ammonia.

Inventors of the present invention have conducted extensive studies to attain the above objects. As a result, they have found that a conspicuously higher yield and selectivity ratio can be attained when a gas-phase catalytic reaction of a heterocyclic carboxylic acid or an ester thereof with ammonia is conducted in the presence of a catalyst comprising an oxide of at least one element selected from copper and zinc.

Inventors of the present invention have further found that, using a heterocyclic nitrile thus produced as a starting material, a heterocyclic aldehyde can be produced effectively.

SUMMARY OF THE INVENTION

The present invention provides a method for producing a heterocyclic nitrile by a gas-phase catalytic reaction of a heterocyclic carboxylic acid or an ester thereof with ammonia in the presence of a catalyst comprising an oxide of at least one element selected from copper and zinc.

The present invention also provides a method for producing a heterocyclic aldehyde comprising a gas-phase catalytic reaction of a heterocyclic carboxylic acid or an ester thereof with ammonia in the presence of a catalyst comprising an oxide of at least one element selected from copper and zinc for producing a heterocyclic nitrile, and a catalytic hydrogenation of the heterocyclic nitrile thus produced in the presence of a hydrogenation catalyst.

EMBODIMENTS OF THE INVENTION

In the present invention, a heterocyclic carboxylic acid or an ester thereof is used as a starting material. The heterocyclic carboxylic acid usable in the present invention is a compound having a heterocycle containing at least one atom selected from a nitrogen atom, a sulfur atom and an oxygen atom as a hetero atom, and at least one carboxyl group bonded to a carbon atom in the heterocycle. Preferably, the heterocyclic carboxylic acid contains a nitrogen atom as the hetero atom in the heterocycle. Examples of the heterocycle include pyrrole ring, imidazole ring, imidazoline ring, pyrazole ring, pyridine ring, pyrimidine ring, quinoline ring, oxazine ring, pyrazine ring, triazine ring and azepine ring. Particularly preferred is a nitrogen-containing heterocyclic carboxylic acid in which the heterocycle contains only one carboxyl group and only one or two nitrogen atoms as the hetero atom, such as pyridine carboxylic acid, pyrazine carboxylic acid and pyrimidine carboxylic acid. The heterocyclic carboxylic acid in the present invention includes an acid anhydride thereof.

Examples of the ester of heterocyclic carboxylic acid usable in the present invention include an alkyl ester of heterocyclic carboxylic acid as described above. The alkyl in the alkyl ester is not particularly limited. Examples thereof include a straight chain or branched alkyl having one to four carbon atoms. Among them. methyl and ethyl are preferred.

In the method of the present invention, a catalyst comprising an oxide of at least one element selected from copper and zinc is used. The oxide of at least one element selected from copper and zinc include a copper oxide, a zinc oxide, a complex oxide of copper and zinc, and a mixture thereof. Preferably, the catalyst comprises an oxide of copper and an oxide of zinc, that is, it comprises a mixture of a copper oxide and a zinc oxide, a complex oxide of copper and zinc, or a mixture thereof. The weight ratio of copper and zinc in the catalyst containing both copper and zinc is preferably 0.05–99.5:1, more preferably 0.2–8.0:1 in terms of the ratio of copper oxide and zinc oxide.

The catalyst used in the present invention may further comprise an oxide of a metal other than copper and zinc as an additional ingredient or a promoter as long as it does not inhibit the gas-phase catalytic reaction of the present invention. Examples of the metal other than copper and zinc include barium, chromium and molybdenum, although the metal is not limited to them.

The catalyst used In the present invention can be produced according to a conventional known method for producing metal oxide catalysts. An oxide of at least one element selected from copper and zinc which is available on the market can also be used, as it is, as the catalyst usable in the present invention. The catalyst is molded into a desired shape, such as powder, column, cylinder, sphere, tablet, to be used in the gas-phase catalytic reaction of the present invention.

Copper compounds and zinc compounds usable as a starting material for producing the catalyst in the present invention are not particularly limited. Examples thereof include complexes, acetates, carbonates, halides, hydroxides, nitrides, ammonium salts, phosphates, sulfates, oxalate, lactates, formates and oxides of copper and zinc.

An oxide of an element selected from copper and zinc can be used as the catalyst as it is. The oxide may be supported on an inert carrier commonly used as a carrier for a conventional catalyst. Examples of the carrier include oxides of silicon, titanium, zirconium or aluminum. Among them an oxide of silicon is particularly preferred.

The gas-phase catalytic reaction of the present invention is usually conducted by feeding a heterocyclic carboxylic acid or an ester thereof and ammonia in a reactor where a catalyst described above has already been charged. (Hereinafter, the term "heterocyclic carboxylic acid" includes not only a heterocyclic carboxylic acid but also an ester.) Amount of ammonia is usually about 1–100 mol, preferably 2–20 mol, per 1 mol of the heterocyclic carboxylic acid.

When a heterocyclic carboxylic acid having a high melting point, such as pyridine carboxylic acid, is used in the present invention, it is preferred that the heterocyclic carboxylic acid is dissolved in a suitable solvent. since it can be easily fed in a reactor with a simple apparatus and a simple operation. The solvents is stable during the gas-phase catalytic reaction of the present invention and inert against the heterocyclic carboxylic acid, ammonia and heterocyclic nitrile. For example, when the heterocyclic carboxylic acid is a nitrogen-containing heterocyclic carboxylic acid, such as pyridine carboxylic acid, or an ester thereof, water, pyridine bases such as pyridine, 2-picoline, 3-picoline and 4-picoline, aromatic hydrocarbons such as toluene and xylene, and the like can be used as the suitable solvent. The solvent is used in an amount so that content of the heterocyclic carboxylic acid in the solution is usually 5–70% by weight, preferably 10–30% by weight.

In the gas-phase catalytic reaction of the present invention, an inert gas such as nitrogen, helium and water vapor may be used as a diluent. Among the inert gas, nitrogen is preferred. When a diluent is used, amount of the diluent is usually 0.1–100 mol, preferably 1–40 mol per 1 mol of the heterocyclic carboxylic acid.

The gas-phase catalytic reaction of the present invention can be conducted in either a fixed-bed reactor or a fluidized-bed reactor. When a fixed-bed reactor is used, the catalyst of the present invention is packed in a reactor tube and the portion in the tube where the catalyst is packed (catalyst packed portion) is heated usually at 250–550° C., preferably at 300–500° C. Thereafter, a heterocyclic carboxylic acid or a solution dissolving a heterocyclic carboxylic acid in a solvent and ammonia, and a diluent if required, are fed to the catalyst packed portion to conduct a gas-phase catalytic reaction. Liquid hourly space velocity of the heterocyclic carboxylic acid (hereinafter, referred to as LHSV) is usually 0.001–5.0 g/(ml–catalyst·hr), preferably 0.01–2.0 g/(ml–catalyst·hr). Space velocity of the mixed gas of a heterocyclic carboxylic acid, ammonia and optional ingredients, that is solvent and diluent (hereinafter, referred to as SV) is usually 30–10000 hr$^{-1}$, preferably 50–1000 hr$^{-1}$. The reaction of the present invention may be conducted under a reduced pressure, atmospheric pressure or an elevated pressure.

The heterocyclic nitrile obtained by the reaction of the present invention can be isolated, for example, according to the following method.

A reaction product gas containing a heterocyclic nitrile exited from a reactor is cooled to obtain a condensate containing a heterocyclic nitrile, or the generated gas is introduced in a suitable solvent to obtain a solution containing a heterocyclic nitrile. From the condensate or the solution, the heterocyclic nitrile can be isolated through a combination of unit operations such as concentration and distillation.

Using a heterocyclic nitrile of the present invention as a starting material, a heterocyclic aldehyde can be produced effectively.

That is, a heterocyclic aldehyde can be produced by a method comprising a gas-phase catalytic reaction of a heterocyclic carboxylic acid or an ester thereof with ammonia in the presence of a catalyst comprising an oxide of at least one element selected from copper and zinc to produce a heterocyclic nitrile, and
a catalytic hydrogenation of the heterocyclic nitrile thus produced in the presence of a hydrogenation catalyst and an acid in an aqueous solvent.

The catalytic hydrogenation of the heterocyclic nitrile can be conducted by charging a heterocyclic nitrile, an aqueous solvent and a hydrogenation catalyst, and a copper salt if required, to a reactor, and then conducting the reaction while stirring and feeding hydrogen gas to maintain the hydrogen pressure at $1.0 \times 10^5$–$2.0 \times 10^6$ Pa, preferably at $5.0 \times 10^5$–$1.0 \times 10^6$ Pa. The reaction temperature is usually at 10–50° C., preferably at 20–40° C. In the reaction above, when absorption amount of hydrogen exceeds about 1.1 times of theory, usually the absorption rate of hydrogen becomes lowering. Then, feed of the hydrogen gas is stopped, and the reaction is terminated.

Examples of the hydrogenation catalyst used in the present invention include Raney catalyst such as Raney nickel and Raney cobalt, rare metal catalyst such as ruthenium/carbon, rhodium/carbon and platinum/carbon, and the like.

A hydrogenation catalyst treated with a copper salt can also be used. In the case where a hydrogenation catalyst treated with a copper salt is used, production of by-products can be suppressed and yield of the heterocyclic aldehyde can be improved, comparing to the case where a hydrogenation catalyst not treated with a copper salt is used.

Among the hydrogenation catalysts, Raney nickel and Raney nickel treated with a copper salt are particularly preferred. As the copper salt, an aqueous solution of a copper salt is preferred. Examples of the copper salt include copper sulfate, copper hydroxide, copper acetate and hydrates thereof. Amount of the copper salt used for treating the hydrogenation catalyst is usually 10–80% by weight, preferably 20–70% by weight, based on the amount of the hydrogenation catalyst.

The hydrogenation catalyst treated with a copper salt can be easily obtained by various methods. For example, it can be obtained by a method where a hydrogenation catalyst available on the market is dispersed in a copper salt solution and suspended, a method where a copper salt is added on preparing a hydrogenation catalyst according to a conventional method, or the like.

In a method where a suspension of the catalyst obtained, the suspension is left as it is to sediment the catalyst and the supernatant liquid is removed by decantation. Then, water is added to the residue for washing the catalyst. The resulting mixture is stirred, then left as it is, followed by decantation to remove the supernatant liquid. These steps for washing the catalyst are repeated for several times to obtain a hydrogenation catalyst treated with a copper salt.

In the catalytic hydrogenation of the heterocyclic nitrile, amount of the hydrogenation catalyst is usually 1–50 parts by weight, preferably 5–30 parts by weight, per 100 parts by weight of the heterocyclic nitrile.

Even when the catalytic hydrogenation is conducted by using a hydrogenation catalyst not treated with a copper salt, if a copper salt is added to the reaction system, production of by-products can be suppressed and yield of the heterocyclic aldehyde can be improved, as the case where a hydrogenation catalyst treated with a copper salt is used.

In the catalytic hydrogenation of the heterocyclic nitrile in the method of the present invention for producing a heterocyclic aldehyde, an acid is used for neutralizing ammonia produced in the reaction. As the acid, either an inorganic acid or an organic acid can be used. Examples of the inorganic acid include sulfuric acid and phosphoric acid, and examples of the organic acid include acetic acid. The acid is used in an amount sufficient for neutralizing the produced ammonia. Since 1 mol of ammonia is produced from 1 mol of the heterocyclic nitrile, amount of the acid is 1 equivalent or more, preferably 1–3 equivalents, per 1 mol of the heterocyclic nitrile.

If the amount of acid is smaller than 1 equivalent neutralization of ammonia becomes insufficient and yield of the heterocyclic aldehyde lowers due to the reaction of the ammonia and the heterocyclic aldehyde.

In the catalytic hydrogenation of the heterocyclic nitrile, 1 mol of water is reacted with 1 mol of the heterocyclic nitrile. Therefore, the reaction is conducted in the presence of water in an amount of 1 mol or more per 1 mol of the heterocyclic nitrile. Usually, water is used as the reaction solvent although a mixture of water of the required amount and a water soluble solvent can be used. Examples of the water soluble solvent include alcohol such as methanol and ethanol. Amount of the aqueous solvent, water or a mixed solvent containing water, is usually 1–15 parts by weight, preferably 3–13 parts by weight, per 1 part by weight of the heterocyclic nitrile.

The heterocyclic aldehyde produced in the reaction can easily isolated and purified by removing the catalyst by filtration of the reaction mixture after termination of the reaction and adding an alkali to the filtrate for neutralization, followed by an extraction, distillation or the like.

The following examples further illustrate the present invention in more detail. The examples should not be construed to limit the scope of the present invention.

In the examples, conversion, yield and selectivity ratio are calculated according to the following definitions.

Conversion (%)={(molar amount of reacted heterocyclic carboxylic acid)/(molar amount of fed heterocyclic carboxylic acid)}·100

Yield (%)={(molar amount of a product, e.x. heterocyclic nitrile. produced by the reaction)/(molar amount of fed heterocyclic carboxylic acid)}·100 selectivity ratio(%)={(molar amount of a product, e.x. heterocyclic nitrile, produced by the reaction)/(molar amount of reacted heterocyclic carboxylic acid)}·100.

EXAMPLE 1

As a catalyst, tablet of copper oxide and zinc oxide (6.4 mm≧3.2 mm, copper oxide/zinc oxide=33/65 by weight) was used. In a reactor made of Pyrex glass and having the inside diameter of 18 mm was packed 14.0 ml of the catalyst, and the catalyst packed portion of the reactor was heated to 320° C. To the catalyst packed portion, a mixture of methyl 6-methylnicotinate and toluene in a molar ratio of 1:4 and ammonia were fed at feeding rates of 0.07 g/minute and 6.3 ml/minute (2 times in mol of the feeding rate of methyl 6-methylnicotinate), respectively. The reaction product gas exited from the reactor tube was introduced in 100 ml of ethanol for 25 minutes to dissolve soluble ingredients contained in the generated gas in the ethanol. The solution thus obtained was analyzed with a gas-chromatography. From the analysis results, the following results were obtained. %

| Conversion of methyl 6-methyl nicotinate | 82.1 |
| --- | --- |
| Yield of 2-methyl-5-cyano-pyridine | 67.9% |
| Selectivity ratio of 2-methyl-5-cyano-pyridine | 82.7% |
| Yield of 2-picoline | 3.3% |
| Selectivity ratio of 2-picoline | 4.1%. |

Recovering ratio of toluene was 93.7%.

EXAMPLE 2

The same reaction and analysis as in Example 1 were conducted except that a feeding rate of ammonia was changed to 12.6 ml/minute (4 times in mol of the feeding rate of methyl 6-methylnicotinate). From the analysis results, the following results were obtained.

| Conversion of methyl 6-methyl nicotinate | 90.2% |
| --- | --- |
| Yield of 2-methyl-5-cyano-pyridine | 78.1% |
| Selectivity ratio of 2-methyl-5-cyano-pyridine | 86.6% |
| Yield of 2-picoline | 2.1% |
| Selectivity ratio of 2-picoline | 2.4%. |

Recovering ratio of toluene was 93.3%.

EXAMPLE 3

The same reaction and analysis as in Example 1 were conducted except that a feeding rate of ammonia was changed to 25.2 ml/minute (8 times in mol of the feeding rate of methyl 6-methylnicotinate). From the analysis results, the following results were obtained.

| Conversion of methyl 6-methyl nicotinate | 96.5% |
| --- | --- |
| Yield of 2-methyl-5-cyano-pyridine | 83.9% |
| Selectivity ratio of 2-methyl-5-cyano-pyridine | 86.9% |
| Yield of 2-picoline | 0% |
| Selectivity ratio of 2-picoline | 0%. |

Recovering ratio of toluene was 91.6%.

EXAMPLE 4

As a catalyst, tablet of copper oxide and zinc oxide (6.4 mm×3.2 mm, copper oxide/zinc oxide=42/47 by weight) was used. In a reactor made of Pyrex glass and having the inside diameter of 18 mm was packed 14.0 ml of the catalyst, and the catalyst packed portion of the reactor was heated to 320° C. To the catalyst packed portion, a mixture of methyl 6-methylnicotinate and toluene in a molar ratio of 1:4 and ammonia were fed at feeding rates of 0.07 g/minute and 6.3 ml/minute (2 times in mol of the feeding rate of methyl 6-methylnicotinate), respectively. The reaction product gas exited from the reactor tube was introduced in 100 ml of ethanol for 25 minutes to dissolve soluble Ingredients contained in the generated gas in the ethanol. The solution thus obtained was analyzed with a gas-chromatography. From the analysis results, the following results were obtained.

| Conversion of methyl 6-methyl nicotinate | 96.5% |
| --- | --- |
| Yield of 2-methyl-5-cyano-pyridine | 79.3% |
| Selectivity ratio of 2-methyl-5-cyano-pyridine | 82.2% |
| Yield of 2-picoline | 6.9% |
| Selectivity ratio of 2-picoline | 7.2%. |

Recovering ratio of toluene was 95.0%.

EXAMPLE 5

In an autoclave were charged 59.1 g (0.50 mol) of 2-methyl-5-cyanopyridine, 245.0 g (0.75 mol as sulfuric acid) of 30% aqueous sulfuric acid solution, 5.9 g of Raney nickel (Catalyst R-101, manufactured by Nikkou Rika Co., Ltd.) and 1.8 g of copper sulfate pentahydrate. Keeping the hydrogen-pressure at 0.7 M Pa by feeding hydrogen from an inlet tube into the autoclave, reaction was conducted at 35° C. When absorption amount of hydrogen reached to 107–110% of theory, the feed of hydrogen was stopped. The reaction time was 4.5 hours. The catalyst was removed by filtration and the filtrate was analyzed with a high performance liquid chromatography. From the analysis results, the following results were obtained.

| | |
|---|---|
| Yield of 2-methyl-5-pyridinecarbaldehyde | 86.8% |
| Yield of 2-methyl-5-pyridinemethanol | 1.8% |
| Yield of 2-methyl-5-pyridinemethaneamine | 9.8% |

2-methyl-5-cyanopyridine was not detected.

EXAMPLE 6

Example 5 was repeated except that amount of copper sulfate pentahydrate was changed from 1.8 g to 3.6 g. The reaction time was 15 hours.

The following results were obtained.

| | |
|---|---|
| Yield of 2-methyl-5-pyridinecarbaldehyde | 83.9% |
| Yield of 2-methyl-5-pyridinemethanol | 3.2% |
| Yield of 2-methyl-5-pyridinemethaneamine | 9.8% |

2-methyl-5-cyanopyridine was not detected.

EXAMPLE 7

Under nitrogen atmosphere, 8.36 g of Raney nickel (Catalyst R-101, manufactured by Nikkou Rika Co., Ltd.) was added to 250 g of 1% by weight aqueous solution of copper sulfate pentahydrate, and the resulting mixture was stirred for 30 minutes at room temperature. Then, the mixture, suspension, was left as it was to sediment the catalyst and the supernatant liquid was removed. The catalyst was washed by adding 100 ml of water to the residue, stirring the resulting mixture, then leaving it as it was to sediment the catalyst and removing the supernatant liquid. This washing step was repeated 5 times in total to obtain Raney nickel catalyst treated with a copper salt solution.

In an autoclave were charged 83.6 g (0.70 mol) of 2-methyl-5-cyanopyridine, 514.6 g (1.05 mol as sulfuric acid) of 20% aqueous sulfuric acid solution, 8.36 g of the Raney nickel catalyst treated with a copper salt solution obtained above. Keeping the hydrogen-pressure at 0.7 M Pa by feeding hydrogen from an inlet tube into the autoclave, reaction was conducted at 25° C. When absorption amount of hydrogen reached to 112% of theory, the feed of hydrogen was stopped to terminate the reaction. The reaction time was 9.5 hours. The catalyst was removed by filtration and the filtrate was analyzed with a high performance liquid chromatography. From the analysis results, the following results were obtained.

| | |
|---|---|
| Yield of 2-methyl-5-pyridinecarbaldehyde | 84.1% |
| Yield of 2-methyl-5-pyridinemethanol | 0.5% |
| Yield of 2-methyl-5-pyridinemethaneamine | 5.0% |

2-methyl-5-cyanopyridine was not detected.

What is claimed is:

1. A method for producing a heterocyclic nitrile comprising
   (a) performing a gas phase catalytic reaction of a heterocyclic carboxylic acid having a pyridine ring, a pyrimidine ring, a quinoline ring, a pyrazine ring or a triazine ring, or an ester thereof with ammonia in the presence of a catalyst comprising an oxide of at least one element selected from copper and zinc.

2. The method according to claim 1 wherein the catalyst comprises a mixture of a copper oxide and a zinc oxide, a complex oxide of copper and zinc, or a mixture thereof.

3. The method according to claim 2, wherein the weight ratio of copper and zinc in the catalyst is 0.05:1 to 99.5:1 in terms of the ratio of copper oxide to zinc oxide.

4. A method for producing a heterocyclic aldehyde comprising:
   (a) performing a gas phase catalytic reaction of a heterocyclic carboxylic acid having a pyridine ring, a pyrimidine ring, a quinoline ring, a pyrazine ring or a triazine ring, or an ester thereof with ammonia in the presence of a catalyst comprising an oxide of at least one element selected from copper and zinc for producing a heterocyclic nitrile; and
   (b) conducting a catalytic hydrogenation of the heterocyclic nitrile in the presence of a hydrogenation catalyst and an acid in an aqueous solvent.

5. The method according to claim 4 wherein the catalytic hydrogenation is conducted in the presence of a copper salt.

6. The method according to claim 4 wherein the hydrogenation catalyst is Raney nickel.

7. The method according to claim 6 wherein the Raney nickel is treated with a copper salt.

* * * * *